(12) United States Patent
Dallas et al.

(10) Patent No.: US 8,113,681 B2
(45) Date of Patent: Feb. 14, 2012

(54) BLOOD TRACKING SYSTEM

(75) Inventors: Edgar A. Dallas, Beaverton, OR (US); Benjamin J. Nyssen, Tigard, OR (US)

(73) Assignee: Fiskars Brands, Inc., Madison, WI (US)

( * ) Notice: Subject to any disclaimer, the term of this patent is extended or adjusted under 35 U.S.C. 154(b) by 303 days.

(21) Appl. No.: 12/422,106

(22) Filed: Apr. 10, 2009

(65) Prior Publication Data

US 2009/0237920 A1 Sep. 24, 2009

Related U.S. Application Data

(63) Continuation-in-part of application No. 11/929,526, filed on Oct. 30, 2007, now Pat. No. 7,517,107, which is a continuation of application No. 11/195,371, filed on Aug. 2, 2005, now Pat. No. 7,290,896.

(60) Provisional application No. 60/598,289, filed on Aug. 3, 2004.

(51) Int. Cl.
*F21L 4/02* (2006.01)

(52) U.S. Cl. .......................... 362/184; 362/231; 362/800

(58) Field of Classification Search .................. 362/184, 362/231, 800

See application file for complete search history.

(56) References Cited

U.S. PATENT DOCUMENTS

| 5,201,755 | A | 4/1993 | Klement |
| 6,019,482 | A | 2/2000 | Everett |
| 7,290,896 | B2 | 11/2007 | Dallas et al. |
| 7,517,107 | B2 | 4/2009 | Dallas et al. |
| 2004/0223342 | A1 | 11/2004 | Klipstein et al. |
| 2006/0044952 | A1* | 3/2006 | Penn et al. .................. 369/30.01 |

* cited by examiner

*Primary Examiner* — Stephen F Husar
*Assistant Examiner* — James Cranson, Jr.
(74) *Attorney, Agent, or Firm* — Foley & Lardner LLP

(57) ABSTRACT

A blood tracking light includes a first light source emitting blue light, a second light source emitting red light, and a third light source emitting cyan light. The light sources combine to create a light beam that provides a distinct visual appearance to blood. The light sources may include one or more LEDs, including blue LEDs, red LEDs, and cyan LEDs. The intensity of the light sources may be varied to enhance the distinct visual appearance of the blood.

20 Claims, 3 Drawing Sheets

BLOOD TRACKING SYSTEM

CROSS-REFERENCE TO RELATED PATENT APPLICATIONS

This application is a continuation-in-part of application Ser. No. 11/929,526, filed Oct. 30, 2007, which is a continuation of application Ser. No. 11/195,371, filed Aug. 2, 2005, which claims the benefit of Provisional Application No. 60/598,289, filed Aug. 3, 2004, all of which are incorporated herein by reference in their entireties.

BACKGROUND

The present invention relates generally to the field of blood tracking. In particular, the present invention relates to a portable lighting unit configured to track blood using a light emitting diode (LED) illumination system.

There are occasions in which it is useful to be able to easily identify small amounts of blood in a particular environment. For example, a hunter may wound an animal, such as a deer, that runs some distance away from the hunter after being wounded. In such a case, the hunter would like to follow the blood trail in order to find the animal. Small drops of blood can be difficult to see on the ground and on foliage, especially in low light conditions. To aid the hunter, blood tracking systems have been devised that help differentiate the red color of the blood from the rest of the environment. Such systems include the utilization of special filters placed on flashlights and/or special goggles or glasses that highlight the blood.

It would be advantageous to provide a portable lighting device that gives the user true blood tracking capability in low-level lighting conditions by using the optical principle of color enhancement. In particular, it would be advantageous to provide a lighting device that gives a distinct visual appearance to blood without requiring special filters on a light source or requiring the user to wear special glasses or goggles.

SUMMARY

One embodiment of the invention relates to a blood tracking light having a blue LED, a red LED, and a cyan LED. The blue LED, the red LED, and the cyan LED combine to create a light beam that highlights blood.

Another embodiment of the invention relates to a blood tracking light having a first light source emitting blue light, a second light source emitting red light, and a third light source emitting cyan light. The first light source, the second light source, and the third light source combine to create a light beam that provides a distinct visual appearance to blood.

Yet another embodiment of the invention relates to a flashlight. The flashlight includes a first light source emitting light of a first color at a first intensity, a second light source emitting light of a second color at a second intensity, and a third light source emitting light of a third color at a third intensity. The first intensity is greater than either the second intensity or the third intensity. The second intensity and third intensity are approximately the same.

BRIEF DESCRIPTION

Figure 3:
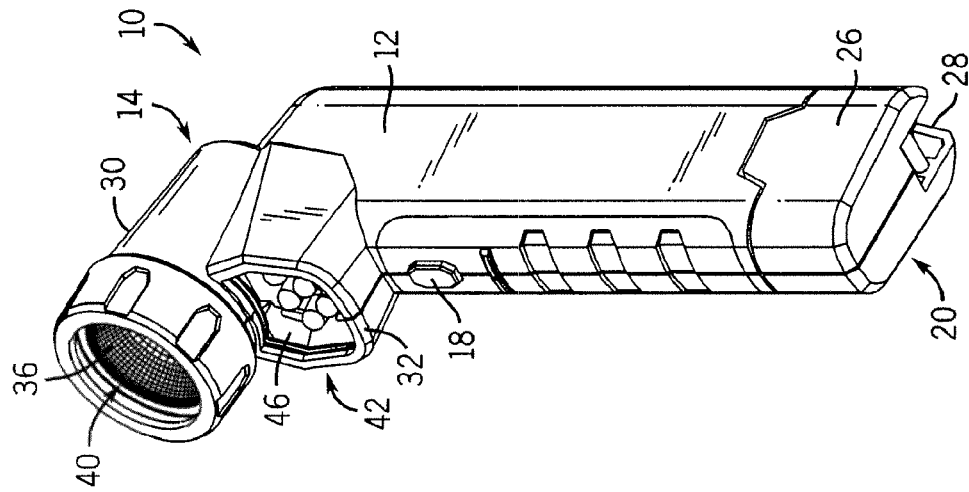
Figure 2:
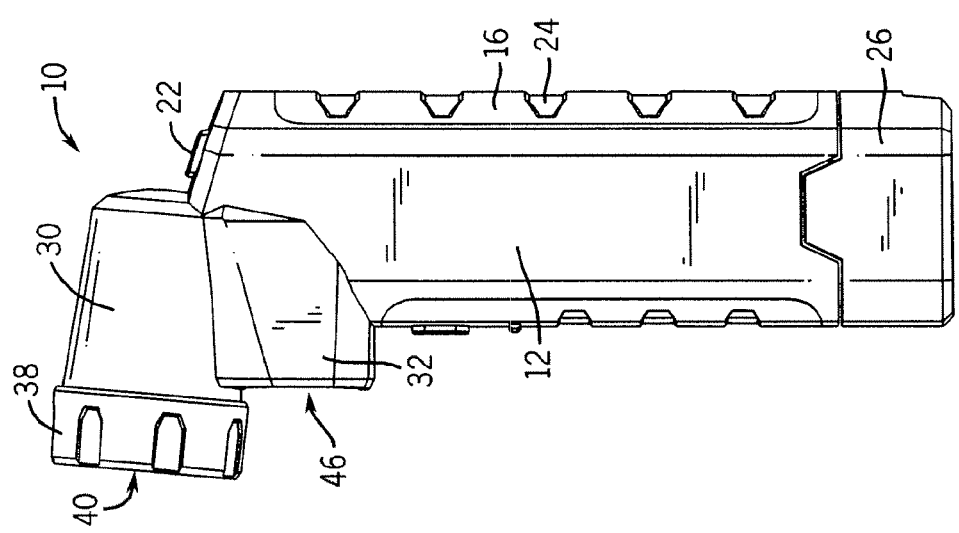
Figure 1:
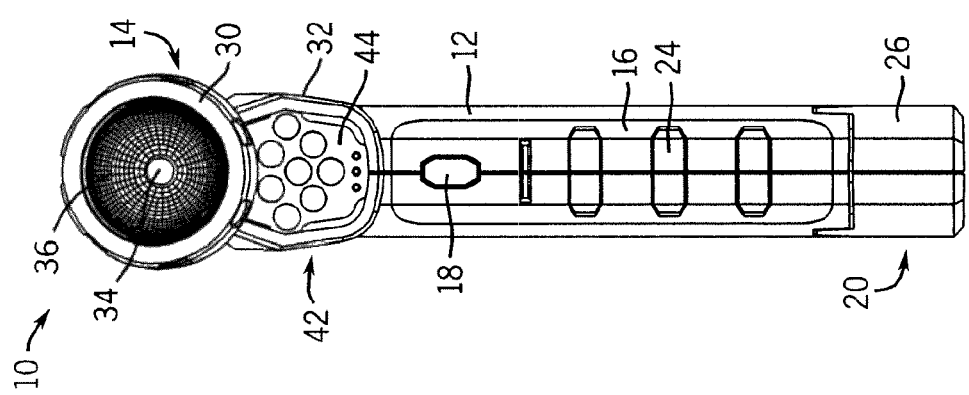
Figure 4:
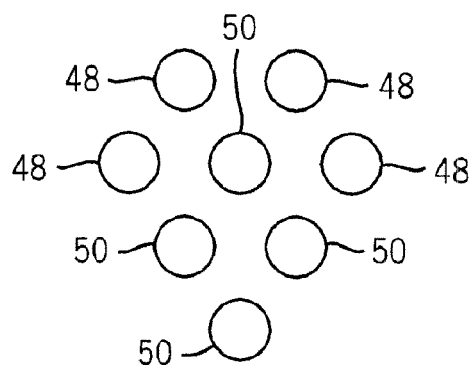
Figure 5:
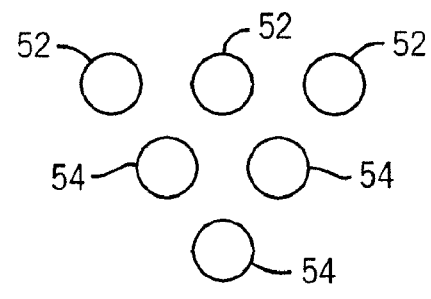
Figure 6:
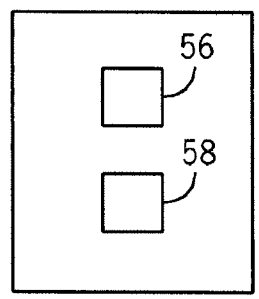
Figure 7:
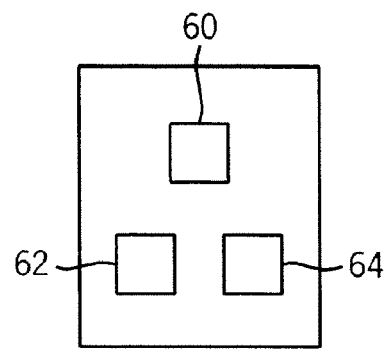
Figure 8:
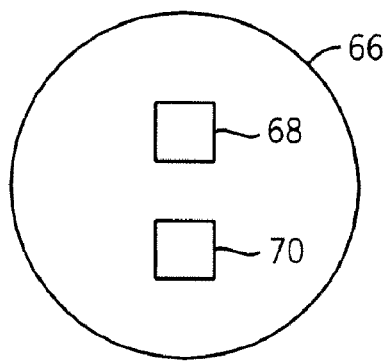
Figure 9:
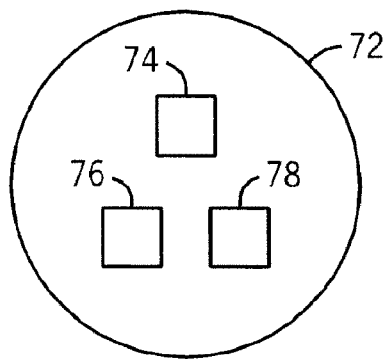
Figure 10:
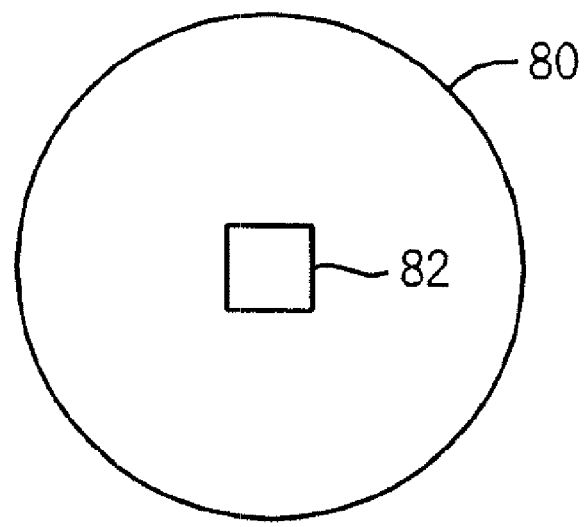
Figure 11:
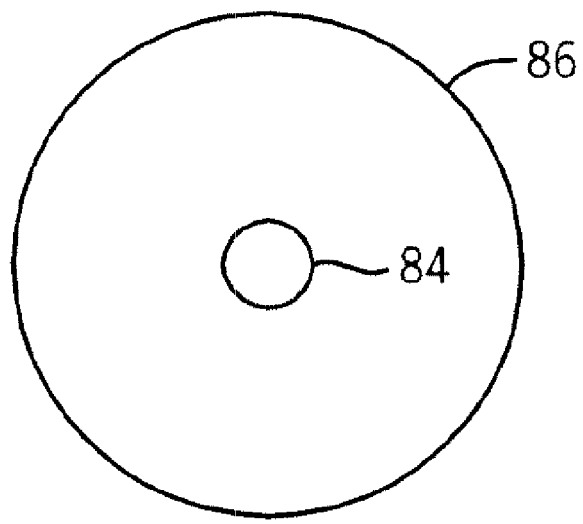

FIG. 1 is a front elevation view of a tracking device.
FIG. 2 is a side elevation view of a tracking device.
FIG. 3 is a perspective view of a tracking device.
FIG. 4 is an elevation view of a LED array.
FIG. 5 is an elevation view of a LED array.
FIG. 6 is an elevation view of a LED array.
FIG. 7 is an elevation view of a LED array.
FIG. 8 is an elevation view of a LED array.
FIG. 9 is an elevation view of a LED array.
FIG. 10 is an elevation view of a LED array.
FIG. 11 is an elevation view of a LED array.

DETAILED DESCRIPTION

Color perception cannot be attributed directly and solely to wavelengths of light. The eye focuses slightly differently on long wavelengths (reds) than on short wavelengths (blues). According to an exemplary embodiment of the present invention, a tracking device may include a multiple color light source having a red LED light beam and a blue LED light beam that create an illusion causing the eye to see red objects in low level lighting conditions as blaze orange. Simultaneously illuminating a red blood spot with the red LED beam and the blue LED beam of the system creates the desired highlighted orange blood effect. The highlighted blood appears orange and the surrounding background green or brown flora appears blue/purple under the multi color LED beam even when the flora is wet.

In an exemplary embodiment, the blood tracking system is incorporated into a portable light source, such as a headlamp flashlight. The headlamp may have a removable, adjustable headband. The headlamp may utilize a single AAA battery to provide power to the LEDs. Alternatively, multiple batteries may be used and the batteries may be of various sizes and types. The blood tracking system may be utilized in other portable light sources such as handheld flashlights and lanterns.

In some embodiments, two distinct colors may be utilized. In an exemplary embodiment, one or more blue LEDs (i.e. LEDs having a peak wavelength centered in the range of about 410 nm to about 500 nm) may be used with one or more red LEDs (i.e. LEDs having a peak wavelength in the range of about 600 nm to about 740 nm) to produce a spot that appears to be magenta to a user. In some embodiments, a LED having an output centered at about 425 nm may be used with an a LED having an output centered at about 625 nm. In another exemplary embodiment, a red LED having a wavelength centered around 628 nm and a blue LED having a wavelength centered around 470 nm may be used.

In some embodiments, the blood tracking system may include two LEDs (a red LED and a blue LED) that are simultaneously activated to provide the desired blood tracking effect. In other embodiments, additional LEDs are used to increase the brightness of the light source, such as two red LEDs and two blue LEDs, or even more LEDs, such as 3-6 red LEDs and 3-6 blue LEDs. The number of red LEDs may be greater or less than the number of blue LEDs. Also, the intensity of the red LEDs may be greater of less than that of the blue LEDs.

In another embodiment, the red LED may be pulsed at a particular frequency, which, when combined with the steady output of the blue LED, can enhance the visual signature of the blood or other red material being tracked.

In some embodiments, the LEDs may be used individually, to provide either red output or blue output separately. In other embodiments, other LEDs may be added to the system, including other LEDs having different colors or wavelengths, such as infrared wavelengths. Circuitry may be utilized to provide different lighting options of the various LEDs and combinations of LEDs.

The tracking device has several potential uses in addition to use in the hunting context described above. For example, the system may have several potential military uses, such as by medics to determine the source of blood on a body that is covered by dirt, mud, or other material obscuring the wound providing the source of blood. Further, special forces personnel may utilize the invention to track enemy combatants that may have been wounded and are providing a blood trail. Also, the tracking device may be used by forensic analysts to find blood.

Referring to FIGS. 1-3, according to an exemplary embodiment, tracking device 10 includes a housing with a handle 12, and a head 14. Handle 12 includes a grip portion 16, first power switch 18, a power supply 20, and a second power switch 22. Head 14 and handle 12 are shown coupled to each other at an angle of about 90° and may be formed as a single unitary body. Alternatively, head 14 and handle 12 may be coupled at other angles or in-line such that the head and handle extend along either the same longitudinal axis, or along longitudinal axes that are substantially parallel. In yet another embodiment, head 14 may be rotatably coupled to handle 12 to allow a user to adjust the angle formed by head 14 and handle 12.

Handle 12 may include a grip portion 16 that includes grooves 24 for the fingers of a user to contact while using tracking device 10. Handle 12 is shown as being generally straight along a longitudinal axis. Alternatively, other ergonomic configurations including a curved handle may be used. Power supply 20 or handle 12 may include a removable cover 26 which may cover a battery compartment. According to some embodiments, tracking device 10 may be adaptable to be used with alternating or direct current from an external power source.

Head 14 may include a primary light source 30 and a secondary light source 32. Primary light source 30 may include a lamp 34, a reflector 36, cap 38, and lens 40. Lamp 34 may be a xenon bulb. Alternatively, lamp 34 may be another type of incandescent bulb, or one or more white LEDs. Reflector 36 may be generally parabolic in shape to direct light emitted from lamp 34 into a beam. Reflector 36 may be faceted or smooth. Primary light source 30 may include a cap 38 for securing the primary light source 30 to head 14. Cap 38 may be threadably or otherwise coupled to head 14. Lens 40 may be disposed within cap 38 to provide a water resistant seal for primary light source 30. According to some embodiments, reflector 36 may be coupled to cap 38 such that rotation of cap 38 moves reflector 36 relative to lamp 34 whereby the width of the light beam produced by primary light source 30 may be adjusted by rotating cap 38. Second power switch 22 may be used to turn primary light source 30 on and off.

Secondary light source 32 may include a LED array 42, shown as eight LEDs of similar size in FIG. 1. A greater or lesser number of LEDs in other configurations may also be used. LED array 42 may be controlled by first power switch 18. In some embodiments, first power switch 18 may simultaneously deactivate primary light source 30 and activate LED array 42.

In some embodiments, tracking device 10 may optionally include a power indicator 44, shown as three LEDs, that may be used to indicate the strength of batteries used to power tracking device 10. Alternatively, a greater or lesser number of LEDs in other configurations may also be used to indicate battery strength. Also, power indicator 44 may be placed in a variety of positions on tracking device 10. Secondary light source 32 may be covered by lens 46 to protect LED array 42 and power indicator 44.

According to some embodiments, removable cover 26 may include an optional coupling point 28 which may be used to attach a lanyard to tracking device 10. Alternatively, a coupling point for a lanyard may be provided elsewhere on tracking device 10.

Referring to FIG. 4, LED array 42 may include a total of eight LEDs 48 and 50. According to some embodiments, LEDs 48 may be blue while LEDs 50 are red. Alternatively, LEDs 48 may be red while LEDs 50 are blue.

Referring to FIG. 5, a LED array for use in a tracking device may include a total of six LEDs. According to some embodiments, LEDs 52 may be blue while LEDs 54 are red. Alternatively, LEDs 52 may be red while LEDs 54 are blue.

Referring to FIG. 6, a LED array for use in a tracking device may include LED dies (i.e. components made of a semiconductor material used to generate light in a LED). According to some embodiments one or more red LED dies 56 may be used with one or more blue LED dies 58. The LED dies may be focused and tuned to produce a homogenous magenta spot.

Referring to FIG. 7, a LED array for use in a tracking device may alternatively include one or more red LED dies 60 may be used with one or more blue LED dies 62 and one or more green LED dies 64 where the green output is kept to a low level relative to the red and blue outputs to avoid diminishing the highlighting effect of the tracking device.

Referring to FIG. 8, a LED array for use in a tracking device may include a bicolor LED 66. According to some embodiments one or more red emitter outputs 68 may be used with one or more blue emitter outputs 70. The LED emitter outputs may be focused and tuned to produce a homogenous magenta spot.

Referring to FIG. 9, a LED array for use in a tracking device may include a tricolor LED 72. According to some embodiments, the tricolor LED 72 may include one or more red emitter outputs 74, one or more blue emitter outputs 76, and one or more green emitter outputs 78. The LED emitter outputs may be focused and tuned to produce a homogenous magenta spot.

Referring to FIG. 10, a LED array for use in a tracking device may include a magenta LED 80. The magenta LED 80 may include an emitter 82 designed to emit a magenta output (i.e. a combination of blue and red wavelengths).

Referring to FIG. 11, a white LED 84 may be used with a filter 86. Filter 86 may absorb green light while transmitting and balancing blue and red light to create a magenta beam. Alternatively, a plurality of filters may be used create a magenta beam. In some embodiments, a plurality of light sources, such as white LEDs may be used with filters to create a magenta beam. For example, one light source including one or more white LEDs and a blue filter may be used with a second light source including one or more white LEDs and a red filter.

According to another exemplary embodiment, the tracking device 10 utilizes three colors to provide the distinct visual appearance to blood. In particular, the tracking device 10 may utilize one or more blue LEDs with one or more red LEDs and one or more cyan LEDs. In a preferred embodiment, the tracking device 10 includes one blue LED, one red LED, and one cyan LED, the combination of the LEDs capable of providing illumination sufficient for blood tracking purposes. According to another embodiment, a single LED array is created with a blue LED die, a red LED die, and a cyan LED die. The use of the blue LED die, the red LED die, and the cyan LED die in a single LED array is advantageous because the light beams from the three LED dies are easier to mix and focus into one beam. In the embodiment using three discrete LEDs, the blue, red, and cyan LEDs may be focused and tuned to produce a homogenous spot using a lens that functions as a color mixer and focusing optic.

Referring back to FIGS. 4 and 5, the LEDs 48, 50 in FIG. 4 and the LEDs 52, 54 in FIG. 5 may be blue LEDs, red LEDs, and cyan LEDs as desired to provide the three color embodiment. Alternatively, referring to FIG. 7, the LED dies 60, 62, and 64 may be blue, red, and cyan to create the LED array. As a further alternative, variable color LEDs (e.g., RGB LEDs) may be utilized along with a controller (e.g. a pulse width modulation controller) configured to control the emitted colors or intensities of the variable color LEDs to provide the blue, red, and cyan light sources that are combined to highlight blood.

According to a preferred embodiment, the cyan LED has a peak wavelength of about 505 nm. The red and blue LEDs may have peak wavelengths in the ranges discussed above, but in a preferred embodiment the blue LED has a peak wavelength of about 470 nm and the red LED has a peak wavelength of about 630 nm.

The addition of the cyan LED is intended to aid in differentiating dried blood from yellow and brown materials that reflect red light to the same extent as dried blood. For example, green leaves tend to absorb nearly all incident red light while fresh blood tends to reflect red light, causing the fresh blood to be highlighted relative to the green leaves. However, as leaves die and turn yellow, brown, and shades of red, they begin reflecting red light to a much greater extent than green leaves. While fresh blood still reflects red light to a much greater extent than the dead leaves, dried blood exhibits much less reflectivity of red light and can be difficult to distinguish from dead leaves (and other non-green forest materials having red tones) when only red and blue light sources are utilized in combination. Adding a cyan light source provides additional highlighting of blood, in particular, dried blood, relative to dead leaves and other non-green forest materials.

The intensity of the individual light sources in the tracking device 10 may be varied to improve the highlighting of blood. In the three color embodiments discussed above, when the tracking device 10 is activated, the luminous intensity (candelas) of the blue and cyan light sources may be greater than the intensity of the red light source. In one embodiment, the number of blue and cyan LEDs is greater than the number of red LEDs to provide the greater intensity of the blue and cyan light sources. In another embodiment, more current is provided to the blue and cyan LEDs to increase their intensity relative to the red LED. In a preferred embodiment, the intensity of the blue and cyan light sources is approximately the same and both have an intensity much greater than that of the red light source. For example, the ratio of the intensity of either the blue LED or the cyan LED to the intensity of the red LED may be ten to one in one embodiment. The increased intensity of the blue LED and the cyan LED relative to the red LED may be accomplished via the selection of appropriate LED sizes or providing the necessary forward current to the LEDs to accomplish the intensity differential.

While the detailed drawings and specific examples given describe various exemplary embodiments of the blood tracking system, they serve the purpose of illustration only. It is to be understood that the invention is not limited in its application to the details of construction and the arrangements of components set forth in the preceding description or illustrated in the drawings. For example, other arrangements of LEDs may be used to create the desired blood tracking effect, or the flashlight may be one of a variety of configurations known in the art. Furthermore, other substitutions, modifications, changes, and omissions may be made in the design, operating conditions, and arrangements of the exemplary embodiments without departing from the scope of the invention as expressed in the appended claims.

What is claimed is:

1. A blood tracking light, comprising:
   a blue LED;
   a red LED; and
   a cyan LED;
   wherein the blue LED, the red LED, and the cyan LED combine to create a light beam that highlights blood.

2. The blood tracking light of claim 1, wherein the blue LED has a peak wavelength in the range of about 410 nm to about 500 nm.

3. The blood tracking light of claim 2, wherein the red LED has a peak wavelength in the range of about 600 nm to about 740 nm.

4. The blood tracking light of claim 3, wherein the red LED is pulsed to further enhance the visual appearance of blood.

5. The blood tracking light of claim 1, wherein the cyan LED has a peak wavelength of about 505 nm.

6. The blood tracking light of claim 1, further comprising an emitter of white light.

7. The blood tracking light of claim 1, wherein when the blood tracking light is activated, the blue LED and the cyan LED have an intensity that is greater than the intensity of the red LED.

8. The blood tracking light of claim 1, further comprising a plurality of additional blue LEDs.

9. A blood tracking light, comprising:
   a first light source emitting blue light;
   a second light source emitting red light; and
   a third light source emitting cyan light;
   wherein the first light source, the second light source, and the third light source combine to create a light beam that provides a distinct visual appearance to blood.

10. The blood tracking light of claim 9, wherein the first, second, and third light sources are LEDs.

11. The blood tracking light of claim 10, wherein the first, second, and third light sources are variable color LEDs.

12. The blood tracking light of claim 11, wherein the second light source is pulsed to further enhance the visual appearance of blood.

13. The blood tracking light of claim 11, wherein the third light source is a LED having a peak wavelength of about 505 nm.

14. The blood tracking light of claim 9, wherein the first light source and the third light source have an intensity that is greater than the intensity of the second light source.

15. A flashlight, comprising:
   a first light source emitting light of a first color at a first intensity;
   a second light source emitting light of a second color at a second intensity; and
   a third light source emitting light of a third color at a third intensity;
   wherein the second intensity is less than either the first intensity or the third intensity and wherein the first intensity and the third intensity are approximately the same.

16. The flashlight of claim 15, wherein the first intensity and the third intensity are greater than ten times the second intensity.

17. The flashlight of claim 16, wherein the first intensity and the third intensity are greater than twenty times the second intensity.

18. The flashlight of claim 15, wherein first color is blue, the second color is red, and the third color is cyan.

19. The flashlight of claim 18, wherein the first light source is a blue LED, the second light source is a red LED, and the third light source is a cyan LED.

20. The flashlight of claim 19, wherein the cyan LED has a peak wavelength of about 505 nm.

* * * * *